United States Patent [19]

Mergler et al.

[11] Patent Number: 4,914,151

[45] Date of Patent: Apr. 3, 1990

[54] RESIN-LINKER COMBINATION FOR THE SOLID-PHASE SYNTHESIS OF PEPTIDES AND INTERMEDIATES

[75] Inventors: Monika Mergler, Liestal; Jacques Gosteli, Basel; Peter Grogg, Bubendorf, all of Switzerland

[73] Assignee: Bachem Feinchemikalein A.G., Switzerland

[21] Appl. No.: 329,985

[22] Filed: Mar. 29, 1989

Related U.S. Application Data

[62] Division of Ser. No. 189,294, May 2, 1988, Pat. No. 4,831,084.

[30] Foreign Application Priority Data

May 18, 1987 [CH] Switzerland .......................... 872/87

[51] Int. Cl.$^4$ ...................... C08L 89/00; C08F 283/00; C08K 283/00
[52] U.S. Cl. .............................. 525/54.1; 525/54.11; 530/333; 530/334; 530/815
[58] Field of Search .................. 525/54.1, 54.11; 530/333, 334, 815

[56] References Cited

U.S. PATENT DOCUMENTS

| | | | |
|---|---|---|---|
| 4,085,261 | 4/1978 | Patchornik et al. | 525/377 |
| 4,173,693 | 11/1979 | Au et al. | 525/381 |
| 4,446,285 | 5/1984 | Parker | 525/383 |
| 4,725,568 | 2/1988 | Parker et al. | 525/370 |
| 4,755,558 | 7/1988 | Kalbag | 525/54.1 |
| 4,762,881 | 8/1988 | Kauer | 525/54.11 |
| 4,764,595 | 8/1988 | Getman et al. | 525/54.11 |
| 4,786,684 | 11/1988 | Glass | 525/54.1 |

FOREIGN PATENT DOCUMENTS 0200404 11/1986 European Pat. Off. .

OTHER PUBLICATIONS

R. B. Merrifield, J. Amer. Chem. Soc., 85, 2149–2154, (1963).
R. C. Sheppard et al., Inter. J. Pept. Prot., Res., 20, 451–454, (1982).
K. D. Kopple, "Peptides and Amino Acids", (W. A. Benjamin, Inc., N.Y.) 1963, pp. 4–7.
S. S. Wang, J. Amer. Chem. Soc., 95, 1328–1333, (1972).
J. Meienhofer et al., Int. J. Pept. Prot. Res., 13, 35–42, (1979).
E. Kaiser et al., Anal. Biochem., 34, 595–598, (1970).

*Primary Examiner*—John Kight
*Assistant Examiner*—Nathan M. Nutter
*Attorney, Agent, or Firm*—Paul & Paul

[57] ABSTRACT

The present invention relates to a novel polymeric carrier, a process for its production and its use for the preparation of peptides and their intermediates. The process comprises reacting chloromethylated polystyrene (cross-linked with divinylbenzene) with a 4-hydroxy-2-substituted-benzyl alcohol (linker), attaching α-amino acids with amino and side-chain protection to the carrier thus obtained, and building up a peptide according to the method known in the field of solid phase peptide synthesis (SPPS). The method allows removal of intermediates or final products under extremely mild acidic conditions giving products in high state of purity and yield. The 2-substituent consists of an electron donating group, such as methoxy.

10 Claims, No Drawings

RESIN-LINKER COMBINATION FOR THE SOLID-PHASE SYNTHESIS OF PEPTIDES AND INTERMEDIATES

CROSS-REFERENCE TO RELATED APPLICATION

This is a divisional application of U.S. patent application Ser. No. 189,294, filed May 2, 1988 and now U.S. Pat. No. 4,831,084.

DESCRIPTION

There are two conventional methods for the synthesis of peptides, the classical, so-called liquid phase synthesis and the solid phase peptide synthesis (SPPS) method developed by R. B. Merrifield (J. Am. Chem. Soc. 85, 2149 [1963]).

The bifunctional nature of the natural α-amino acids requires the use of protecting groups in either method of synthesis. While the liquid phase technique permits the isolation and purification of products after each step, the solid phase method allows for no such intermediary purification. Rather, the final product upon cleavage with a strong acid of protecting groups and resin-carrier has to subjected, due to its low grade, to often cumbersome purification methods. The preparation of intermediates (fragments) still carrying protected functions useful as building blocks (for alternate syntheses for example) is thus impossible. In European Patent Application EPA 0200404 a solid phase synthesis method is described yielding peptide amides on cleavage from the carrier-resin, but unfortunately no acid-sensitive protection groups can be used for the side-chain functions in case protected peptide fragments need to be made.

Surprisingly it has been found the novel polymeric carrier (resin-linker compound) prepared according to the invention, as described herein thereafter, allows for the first time the advantageous cleavage of a peptide in protected form with a free terminal carboxyl group under extremely mild reaction conditions. In other words, the method to be described allows the isolation and preparation of protected intermediates (fragments or building blocks) that can be further processed, by any method of choice, e.g. by the liquid phase peptide synthesis method. The invention relies on the construction of a material on which a growing peptide can be synthesized and from which such peptide (or fragment) can be liberated under so extremely mild acidic conditions, that the protected functions in the side-chains remain unattacked in the cleavage reaction. It should be stressed that such cleavage can be carried out at any stage. This technology boardens the strategic scope of peptide synthesis considerably. Thus, fragments obtained can be readily purified if necessary, and further processed by any method of choice optionally extending the peptide chain further at the carboxyl terminus or at the α-amino end group.

The polymeric resin of formula I

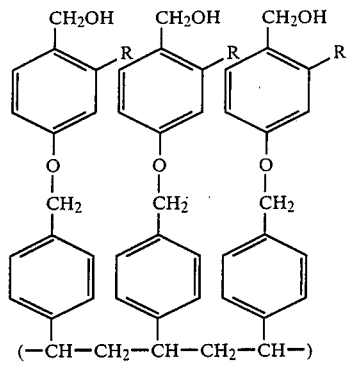

in which R represents a lower alkoxy-, lower alkylthio or a

group, in which $R_1$ and $R_2$ stand for lower alkyl. The polymeric compound is optionally cross-linked with 0.5–2% of divinylbenzene optionally substituted by halogen or lower alkyl.

The term "lower" in connection with organic groups indicates that the groups have up to seven carbon atoms, and preferably up to four carbon atoms. Lower alkoxy is, e.g., methoxy, ethoxy, n-propoxy, isopropoxy, n-hexyloxy, isohexyloxy or n-heptyloxy.

Lower alkylthio stands for, e.g., methylthio, ethylthio, n-propylthio, isobutylthio, tert.-butylthio, n-butylthio, n-pentylthio, n-hexylthio or n-heptylthio, and $R_1$ and $R_2$ as substituents in the lower dialkylamino-group represent methyl, ethyl, n-propyl, isopropyl, n-butyl, isobutyl, sec.-butyl, tert.-butyl, n-pentyl, isopentyl, neopentyl, n-hexyl or n-heptyl and R as diloweralkylamino is for example N,N-dimethylamino, N-ethyl-N-methylamino or N,N-diethylamino. Halogen is for example chlorine, bromine, iodine or fluorine.

A preferred embodiment of the invention are polymeric carriers (resin-linker compounds) derived from a polymer of formula I, in which R represents lower alkoxy and which is crosslinked with 1 to 2% unsubstituted divinylbenzene. Especially of interest are polymeric carriers derived from a polymer of formula I, in which R represents methoxy and which is crosslinked with 1 to 2% unsubstituted 1,4-divinylbenzene.

Polymeric compounds of structure I can be derived by reacting chloromethylated polystyrene (R. B. Merrifield, loc. cit.) of formula II which is crosslinked with 0.5–2% of divinylbenzene optionally substituted by halogen or lower alkyl with a 4-hydroxy-2-substituted benzyl alcohol (called the linker) under basic conditions whereby the phenolic hydroxyl group is etherified to the resin.

Such a linker substance is represented by 4-hyroxy-2-methoxybenzyl alcohol of formula III

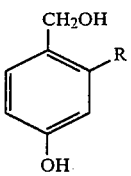

a new compound which can be prepared by reduction of 4-hydroxy-2-methoxybenzaldehyde (3-methoxy-4-formylphenol) the latter compound having been described by R. C. Sheppard and B. Williams, Int. Journ. Pept. Prot. Res. 20, 451 (1982).

The etherification of the phenolic hydroxyl group can be performed in the presence of such a base that forms a salt with said phenolic group as exemplified, e.g., by S. S. Wang in J. Am. Chem. Soc. 95, 1328 (1973).

To the compound thus obtained, consisting of the polymeric carrier, a styrene-divinylbenzene copolymerisate and the linker substance, is attached the carboxy-terminal amino acid of the peptide or peptide fragment to be synthesized. The carboxy-terminal amino acid carrying its amino group is protected form, is attached via ester formation. The masking group for the amino function is preferentially of the king that can be cleaved under basic conditions, i.e. by treatment with a base. The esterification can be effected by known methods via activation of the carboxyl group.

Thus the carboxyl group can for example be converted to an acid azide, anhydride, imidazolide, isoxazolide or an activated ester, or through reaction with a carbodiimide such as N,N'-dicyclohexylcarbodiimide (DCC) to an O-acylisourea. The most commonly used mode consists of the one employing a carbodiimide and a catalyst such as 4-dimethylaminopyridine or N-hydroxysuccinimide. (E. Wünsch: Synthese von Peptiden, Georg Thieme Verlag, Stuttgart 1974 in Houben-Weyl: Methoden der Org. Chemie, 15/I and II, 4th edition).

The amino acid or peptide fragment carrying an amino protecting group is coupled to the carrier resin using, e.g. dicyclohexyl carbodiimide and 4-tert. aminopyridine within 2 to 24 hours, preferably within 12 hours at a temperature of 0° to 50° C., preferably at a temperature of 20° to 25° C., in a solvent such as dichloromethane or dimethylformamide or a mixture of both.

If the amino acid to be condensed, as well as those to be condensed thereafter, bears a functioned group in the side chain, such as a carboxy-, amino-, amido-, hydroxy-, mercapto or guanidino-function, the latter is preferentially protected by such a group, that is resistent to the cleavage reaction of the peptide or fragment from the carrier resin at a later stage. The specific purpose to be achieved determines the appropriate selection of the protection groups for the sidechain functions.

A carboxyl-protecting group is one which is commonly used in peptide chemistry. Such groups are cleavable under mild reaction conditions so as to prevent undesirable side reactions. The cleavage can be effected by solvolysis in acidic or basic medium, by hydrogenolysis, reduction, photolysis or also under physiological conditions. As a rule the carboxyl protection group is replaced by hydrogen. Protecting groups of this kind and their cleavage are described in "Protective Groups in Organic Chemistry", Plenum Press, London, New York, N.Y., 1973 and in "The Peptides", Vol. I, Schröder and Lübke, Academic Press, London, New York, N.Y., 1965, as well as in "Methoden der Organischen Chemie", Houben-Weyl, 4. Auflage, Bd. 15/1, Georg Thieme Verlag, Stuttgart, 1974. In this synthesis method carboxyl groups can be protected, e.g. by esterification. Especially suited for this reaction are lower, substituted alkanols such as 2,2,2-trichloroethanol, tert. butanol, benzoylmethanol or benzyl alcohol.

Specially preferred groups are the tert. butyl group and the benzyl group.

A protecting group for the amino function can be an acyl group, such as an acyl of an aliphatic, aromatic or araliphatic carboxylic acid, especially lower alkanoyl such as acetyl or propionyl, or aroyl such as benzoyl, or formyl or an acyl of a carbonic acid half-ester, such as benzyloxycarbonyl or fluorenylmethyloxycarbonyl (Fmoc).

The cleavage of such an acyl residue serving as protecting group from an amino function can be performed by known methods, such as solvolysis exemplified by alcoholysis. Moreover it can be brought about by hydrolysis in acidic or basic medium. The alcoholytic cleavage of an acyl residue can be effected, e.g. in presence of a basic reagent and/or at elevated temperature, e.g. from 50° C. to 120° C. with a lower alkanol such as n-butanol or ethanol. A base is used hereby such as an alkali metal alcoholate, e.g. sodium or potassium ethoxide or an alkali metal hydroxide, e.g. sodium or potassium hydroxide.

Other aminoprotecting groups, such as lower alkoxy-carbonyl-groups e.g. tert.-butoxycarbonyl, can be cleaved under specially mild acidic conditions, e.g. by treatment with trifluoroacetic acid. Another group, cleavable under especially mild conditions consists of an ethoxycarbonyl group carrying in the $\beta$-positin a silyl group substituted with three hydrocarbon residues, such as triphenylsilyl, dimethyl-butylsilyl or especially trimethylsilyl. These can be cleaved by reaction with fluoride ions, especially fluoride salts of quaternary ammonium bases, such as tetraethylammonium fluoride.

An especially suitable protecting group for the $\alpha$-amino group of the amino acids to be attached to the resin-linker and subsequently to the growing peptide chain is the 9-fluorenylmethyloxycarbonyl (Fmoc) group. It can be cleaved with bases such as alkali hydroxides or carbonates, but especially mildly with organic bases such as piperidine.

For protection of side-chain amino ($\epsilon$-amino) groups any group commonly used in peptide chemistry can be applied. However, in view of the necessity to cleave groups from $\alpha$-amino functions for the propagation of the synthetic sequence it is desirable to choose such groups that are not cleaved when the $\alpha$-amino protecting group is split off. For example, if a group is used for $\alpha$-amino protection which can be removed by base treatment such as the Fmoc-group, then preferentially a group is employed for side-chain amino groups which can be removed upon completion of the synthesis by acidic treatment (orthogonal strategy is a term used in the scientific literature for this methodology). For protection of side chain hydroxyl groups all protecting groups conventionally known to be useful in the peptide field can be used; cf. Houben-Weyl, cited above. Preferred are, however, for the reasons outlined above regarding side chain amino groups, groups clevable by acidolysis. These are, e.g. 2-tetrahydropyranyl and especially tert. butyl and tert. butoxycarbonyl. Besides can be used such groups that are cleavable by reduction such as benyzl and benzyloxy carbonyl or acyl such as acetyl or benzoyl (optionally substituted) that can be removed by solvolysis or hydrogenolysis.

For protection of side chain mercapto groups all usual protecting groups of the peptide field can be applied. In particular the mercapto groups can be blocked by acylation, alkylation or disulfide formation. Preferred mercapto-protecting groups are, for example, benzyl, optionally substituted in the phenyl radical, for example by methoxy or nitro, such as 4-methoxy benzyl, diphenylmethyl optionally substituted in the phenyl moiety, for example by methoxy, such as 4,4-dimethoxy-diphenylmethyl, triphenylmethyl, trimethylethyl, benzylthiomethyl, tetrahydropyranyl, acylaminomethyl, benzoyl, benzyloxycarbonyl or aminocarbonyl, such as ethylaminocarbonyl.

For protection of side chain carboxylic acid amide groups such as occurring in asparagine and glutamine the groups known and commonly used in peptide chemistry may be applied. Particularly such protection is provided by alkylation at the N-atom of the amide function with methoxy-substituted benzyl diphenylmethyl or xanthyl groups all removable by acidolysis in presence or absence of a scavenger suc as anisol.

The guanidino group such as occurring in the side chain of arginine can equally be protected by methods known in the art of peptide synthesis. See, e.g. "Protective groups in Organic Chemistry", Plenum Press, London, New York N.Y. (1973). The protecting groups used here include tosyl, p-methoxy-benzenesulfonyl, 4-methoxy-2,3,6-trimethylbenzenesulfonyl, mesitylenesulfonyl, carbobenzoxy and tert. butoxy carbonyl groups. Deblocking can be performed by acidolysis or hydrogenation.

The compound obtained from the resin-linker with the $N_\alpha$-protected amino acid to be positioned at the carboxy terminus of the target (final) product serves as starting material to any peptide with this amino acid as carboxy terminus. Liberation of the alpha-amino group by cleaving the masking group from the carboxy-terminal amino group to form an intermediate resin-linker followed by coupling of the next amino acid (with $N_{alpha}$-protection) with the intermediate resin linker leads to the growth of the peptide chain. Chain propagation is achieved by removal of the $N_\alpha$-protecting group and attachment of the next amino acid in $N_\alpha$-protected form.

The fragments thus obtained, consisting of the novel resin-linker combination and an amino acid or a peptide are also new and useful as intermediates for further synthesis.

These fragments of general formula IV

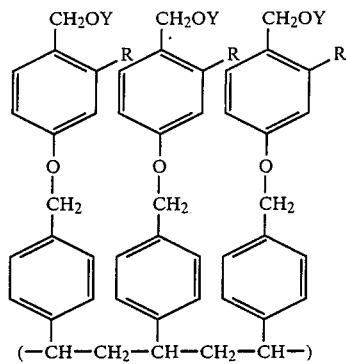

in which R has the meaning as defined under formula I and Y is the residue of an amino acid or a peptide which has been condensed with the terminal carboxyl group to the carrier (ester), the functional groups of the amino acid may optionally be protected, are also a subject of the present invention.

A special embodiment of the invention are fragments of general formula IV in which R represents lower alkoxy, especially methoxy. Removal of the protected peptide from the resin-linker combination can be performed under very mild acidic conditions leaving all other protecting groups intact. The products can be isolated by filtering off the insoluble resin-linker combination and by processing the filtrate according to methods known in the art. The technique allows the synthesis of peptides that consist of 40, 50, 60 or even more amino acids.

All available amino acids such as thse described by K. D. Koppe in "Peptides and Amino Acids" (W. A. Benjamin, Inc., New York, N.Y., 1966 p. 4–7) can serve as building units, especially those naturally occurring in peptides but also their enantiomers (D-series) homologs and isomers. If not indicated otherwise the abbreviations used commonly of the amino acids refer to those of the L-series.

The invention will be illustrated but not restricted by the following examples. Temperatures are given in centigrades, abbreviations are the ones used in the field of peptide synthesis ("Synthesis of peptides", editor-: E. Wünsch, Vol. XV of "Methoden der Org. Chemie", Houben-Weyl, 1974, G. Thieme, Stuttgart, FRG).

EXAMPLE 1

60.85 g of 3-Methoxy-4-formylphenol (R. C. Sheppard and B. Williams, Int. J. Pept. Prot. Res. 20, 451 [1982]) was dissolved under exclusion of air in a mixture of 16.0 g of solid sodium hydroxide, 1200 ml of water and 400 ml of methanol by stirring. 15.13 g of sodium borohydride was added in small portions, while the course of the reaction was being monitored by thin layer chromatography using silicagel plates and the mixture chloroform:methanol-acetic acid=85:10:5 (v/v) as eluant. Stirring is continued for one hour upon completed addition of the reductant. The slightly turbid reaction solution was now diluted with 1,0 l of brine. This was followed by careful addition of potassium hydrogen sulfate, 57.13 g, to the mixture which gradually turned turbid due to the precipitation of the product. This was extracted by two portions of ethyl acetate, 1.5 l each. The pH value of the aqueous phase should be kept at 7 to 8. The extract was shaken with some solid sodium bicarbonate, washed with two 1,0 l portions of brine, dried over sodium sulfate and evaporated in vacuo (part of the product may precipitate during this operation). The crude product of 3-methoxy-4-hydroxymethyl-phenol can be used without further purification for the alkylation reaction (subsequent step). It may, however, be purified by dissolution in a minimum amount of methanol-ethyl acetate (1:1) and dropwise addition of hexane while stirring and cooling. The crystalline product was collected by filtration. Colorless needles, m.p. 128°–130° C. The product is very acid sensitive.

EXAMPLE 2

In this example a poly (chloromethylstyrene-Co-1% divinylbenzene) containing 1.04 meq Cl/g was used. A satisfactory result, however, was also obtained with a resin of 0.67 meq Cl/g. Prior to the reaction the resin, 111.4 g, was preswallen (preferably overnight) in 750 ml of dimethylacetamide (DMA). This solvent previously had been standing over molecular sieves (4 Å) for several days. To the suspension of the resin was added a solution of 3-methoxy-4-hydroxymethylphenol, 55.7 g, in 260 ml of dimethylacetamide. The stirred mixture was gradually heated to 50° C. when sodium methoxide, 19.4 g, was added in portions. Under exclusion of oxygen stirring was continued for 7 hours at the same temperature. The dark red mixture was allowed to cool, water was added to dissolve the precipitated sodium chloride. The resin shrank and its dark color almost faded. It was filtered off and the dark-red filtrate discarded. To swell the obtained polymer p-(3-methoxy-4-hydroxymethyl)-phenoxymethyl) polystyrene the latter was washed three times with either dioxane or tetrahydrofurane. Residual colored impurities were removed by washing 3 times with 50%-aqueous dioxane. To dehydrate the product it was washed with tetrahydrofurane or a mixture of the latter with methanol or diisopropylether. The product thus obtained was almost colorless with a pink or beige shade. Upon drying in vacuo it weighed 130 g. Chlorine content: below 0.1%.

EXAMPLE 3

Coupling of 9-fluorenylmethyloxycarbonyl-alanine (Fmoc-Ala) to the resin obtained in example 2. The resin, 25.32 g, was preswollen by washing several times with dimethylformamide-methylene chloride=1:4 (v/v), then stirred at 0° C. in 100 ml of the same solvent mixture. To the suspension was added Fmoc-Ala, 19.7 g, and 4-dimethylaminopyridine, 0.23 g, as catalyst. Upon stirring for a few minutes dicyclohexyl carbodiimide, 10.74 g, was added in small portions. The mixture was stirred overnight and during this time allowed to reach room temperature. Polymer and formed dicyclohexylurea were filtered off and the latter dissolved by washing five times with a mixture of dimethylformamide and methylene chloride, three times with methylene chloride-isopropanol mixture, methylene chloride and diisopropylether. Finally the resin was dried in vacuo. Fmoc-content: 0.685 milliequivalents (meq) Fmoc-Ala/g (see below). Gravimetric determinations: 0.633 meq Fmoc-Ala/g. Check for racemization: 0.1% D-Ala. Should the loading with the protected amino acid be insufficient, the process can be repeated. Any remaining free hydroxyl groups must at this stage (after the loading) be blocked. The process is also referred to as capping. A suitable reagent herefore is known to be benzoyl chloride. A portion of 35.7 g of the Fmoc-Ala-resin was suspended in 200 ml of methylene chloride. While being chilled in an ice-bath pyridine (18 ml) and a few minutes thereafter benzoylchloride (28 ml) were cautiously added to the mixture. After 30 minutes of stirring the resin was filtered off, washed with methylene chloride, dimethylformamide, isopropanol, diisopropylether and twice with methylene chloride, isopropanol and diisopropylether. Upondrying in vacuo 37.8 g of resin was obtained which was used directly for a peptide synthesis. The polymer was characterized as follows:

($c_1$) Fmoc-determination:

small weighted samples were treated for 30 minutes with piperidine/dimethylformamide=1:4 to cleave the Fmoc group. The concentration of the formed cleavage product 9-fluorenylmethylpiperidine was determined photometrically (301 nm), $\epsilon_m$ 7200)

($c_2$) Gravimetric determination (cleavage of the Fmoc-amino acid):

A weighed sample was treated with a solution of 1% of trifluoroacetic acid in methylene chloride (see below). The resin was washed with methylene chloride and dried. The solution of the Fmoc-amino acid was neutralised and evaporated in vacuo. The residue was dried and weighed. The dried resin was also weighed. This experiment also allowed to determine the cleavage conditions.

($c_3$) Extent of racemization:

A weighed sample was at first treated with piperidinedimethylformamide to remove the Fmoc group. After careful washing it was cleaved with trifluoroacetic acid-methylene chloride 1:1. The cleavage need not be complete. The sample was filtered and washed with methylene chloride and propanol. The filtrate was evaporated several times completely with propanol. The optical purity of the N-trifluoroacetyl-n-propyl-ester of the amino acid was examined using a column filled with a chiral absorbent.

EXAMPLE 4

(a) The syntheses on the acylated polymer are performed according to well described methods of solid-phase peptide synthesis (SPPS) with Fmoc-amino acids, such as published by J. Meierhofer et al., Int. J. Pept. Prot. Res. 13, 35 (1979). The process was monitored with the Kaiser-test (E. Kaiser et al., Anal. Bioch. 34, 595 [1970]) and the Fmoc-determination (see above). Solvents used were dimethylformamide and methylene chloride and their mixtures. The Fmoc-amino acids were used in a twofold or higher excess and activated by dicyclohexylcarbodiimide/4-dimethylaminopyridine.

(b) Cleavage of a fully protected peptide from resin. Prior to the reaction the loaded resin was washed with methylene chloride and stirred for a few hours in the same solvent. Impurities such as water or alcohols interfere with the reaction. Likewise, residual dicyclohexylurea that had not been washed away completely will appear as an impurity in the product and moreover will have consumed a portion of the trifluoroacetic acid used.

(c) Kassinin 1–5

Boc-Asp(OBut)-Val-Pro-Lys(Boc)-Ser(But)OH 12.63 g of the loaded resin was stirred in 100 ml of methylene chloride for 5 hours, when 100 ml of a 2% trifluoroacetic acid solution (in the same solvent) was added. The mixture was stirred for 30 minutes and filtered. The filtered off resin was resuspended in 200 ml of a 1% trifluoroacetic acid solution and stirred for 45 minutes. The resin turned pink-violet during this operation. The process was repeated once more and the three filtrates checked by thin layer chromatography. The bulk of product was contained in the second filtrate. The filtrates were immediately neutralized, pooled and concentrated in vacuo and the distilled off solvent replaced by ethyl acetate. The solution thus obtained was washed with 150 ml of a mixture of 5% sodium bicarbonate solution and brine (2:1). The product remained in the organic phase, which now was washed with 150 ml of a mixture of 1N KHSO₄-solution and brine (2:1) and finally with 100 ml of brine (10% sodium chloride solution). The organic layer was dried over sodium sulfate and evaporated in vacuo. C found 57.06%, H found 8.51%, N found 9.38% C calc 57.37%, H calc 8.58%, N calc 9.80%.

EXAMPLE 5

ANF (atrial naturiuretic factor) 1–10

Boc-Ser(But)-Leu-Arg(Mtr)-Arg(Mtr)-Ser(But)-Ser(But)-Cys(Amc)-Phe-Gly-Gly-OH 5.03 g of the charged resin (peptide resin) was first washed several times with methylene chloride, then stirred with four portions of 100 ml each of a 1% solution of trifluoroacetic acid in methylene chloride for 30 minutes (each time). The first portion contained 0.2 ml of m-cresol. The bulk of the product appeared in the first two portions. The resin was washed with methylene chloride and dried. The four acidic filtrates were neutralized with pyridine and pooled. The solution turned viscous and gel-like. The bulk of the solvent was removed in vacuo and the remaining oily condensate stirred vigorously with diisopropylether. The suspension was stirred with dilute hydrochloric acid to remove pyridine and salts thereof. The peptide product, remaining in suspension was filtered off and washed with water and diisopropylether. 2.43 g of product was obtained. loss from polymer: 2.13 g.

What is claimed is:

1. Peptidylresin fragments consisting of a polymer having the formula IV:

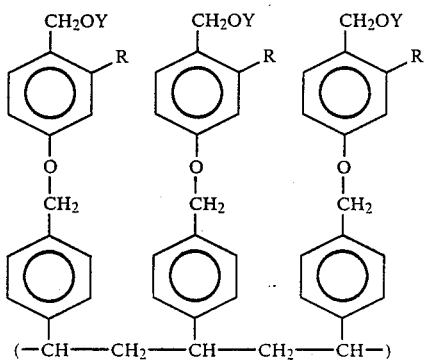

cross-linked with 0.5–2.0% of divinylbenzene optionally substituted by halogen or lower alkyl, in which R represents a lower alkoxy, lower alkylthio or a

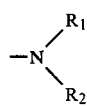

group, in which $R_1$ and $R_2$ stand for lower alkyl, and Y represents the residue of an amino acid or peptide of which the carboxyl group is condensed in ester manner and in which the functional groups may optionally be protected.

2. Fragments according to claim 1 consisting of a polymer of formula IV, in which R is lower alkoxy and Y represents the residue of a naturally occurring α-amino acid or their enantiomers (D-series), homologs and isomers with its functional groups optionally protected.

3. Fragments according to claim 1 consisting of a polymer of formula IV, in which R is methoxy and Y represents the residue of a naturally occurring α-amino acid with its functional groups optionally protected.

4. Fragments according to claim 1 consisting of a polymer of formula IV, in which R is methoxy and Y represents the residue of a naturally occurring α-amino acid and in which the α-amino group is blocked by the Fmoc-group (9-fluorenylmethyloxycarbonyl).

5. A fragment according to claim 1 consisting of a polymer of formula IV, in which R is methoxy and Y represents the Ala-residue.

6. A fragment according to claim 1 consisting of a polymer of formula IV, in which R is methoxy and Y represents the Arg-residue.

7. A fragment according to claim 1 consisting of a polymer of formula IV, in which R is methoxy and Y represents the Asn-residue.

8. A fragment according to claim 1 consisting of a polymer of formula IV, in which R is methoxy and Y represents the Gln-residue.

9. A fragment according to claim 1 consisting of a polymer of formula IV, in which R is methoxy and Y represents the Gly-residue.

10. A process for synthesizing peptides using a peptidylresin consisting of a polymer having the formula:

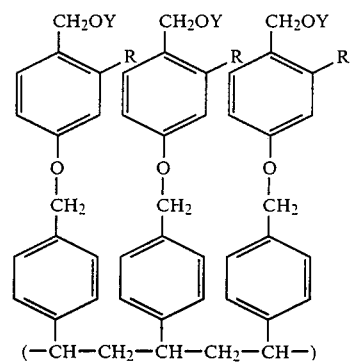

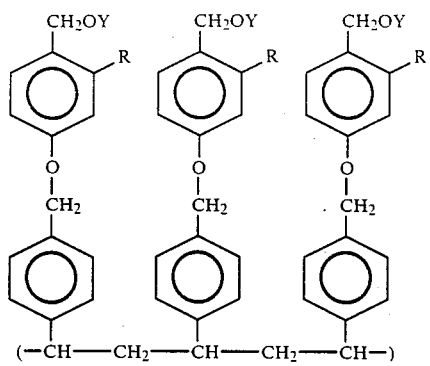

cross-linked with 0.5–2.0% of divinylbenzene, in which R represents a lower alkoxy, lower alkylthio or a

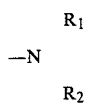

group, in which $R_1$ and $R_2$ stand for lower alkyl, the polymer being cross-linked with 0.5–2.0% divinylbenzene optionally substituted by halogen or lower alkyl, and Y represents the residue of an amino acid or peptide of which the carboxyl group is condensed resin-linker in ester manner and in which the functional groups may optionally be protected, the carboxy-terminal amino group of the residue being protected by a masking group, the process comprising:

cleaving the masking group from the carboxy-terminal amino group to form an intermediate resin linker, and subsequently coupling the intermediate resin linker with an amino acid having a protected carboxy-terminal amino group.

* * * * *

UNITED STATES PATENT AND TRADEMARK OFFICE
CERTIFICATE OF CORRECTION

PATENT NO. : 4,914,151

DATED : April 3, 1990

INVENTOR(S) : Monika Mergler, Jacques Gosteli, and Peter Grogg

It is certified that error appears in the above-identified patent and that said Letters Patent is hereby corrected as shown below:

```
Column 3, line 24, delete "is" and substitute -- in --.
Column 3, line 26, delete "king" and substitute -- kind --.
Column 4, line 35, delete "positin" and substitute --
position --.
Column 5, line 32, delete "suc" and substitute -- such --.
Column 6, line 58, after "methanol", delete " - " and
substitute -- : --.
Column 7, line 23, delete "260" and substitute -- 250 --.
Column 7, line 32, after "hydroxymethyl", delete " ) ".
Column 7, line 60, after "determinations", delete " : ".
Column 8, line 12, delete "weighted" and substitute -- weighed
--.
```

Signed and Sealed this

Fourth Day of June, 1991

*Attest:*

HARRY F. MANBECK, JR.

*Attesting Officer*　　　*Commissioner of Patents and Trademarks*